United States Patent [19]

Kazan

[11] Patent Number: 4,918,199

[45] Date of Patent: Apr. 17, 1990

[54] PROCESS FOR PRODUCING THIOTEPA

[75] Inventor: John Kazan, Martinsville, N.J.

[73] Assignee: American Cyanamid Company, Wayne, N.J.

[21] Appl. No.: 146,511

[22] Filed: Jan. 21, 1988

[51] Int. Cl.$^4$ ............................................. C07D 205/02
[52] U.S. Cl. ...................................... 548/956; 548/969
[58] Field of Search ................................ 548/956, 969

[56] References Cited

U.S. PATENT DOCUMENTS 2,212,146  8/1940  Berchet et al. ...................... 548/969
2,670,347  2/1954  Kuh et al. ........................... 548/956

OTHER PUBLICATIONS

I. Gabriel, Ber., 21, 1049 (1888).
II. Gabriel, Ber., 21, 2664 (1888).

*Primary Examiner*—Mukund J. Shah
*Assistant Examiner*—C. L. Cseh
*Attorney, Agent, or Firm*—Kenneth J. Dow

[57] ABSTRACT

This disclosure describes an improved process for preparing N,N', N"-triethylenethiophosphoramide by the in situ generation of ethyleneimine.

1 Claim, No Drawings

PROCESS FOR PRODUCING THIOTEPA

DETAILED DESCRIPTION OF THE INVENTION

This invention relates to an improvement in the process for producing the antineoplastic agent THIOTEPA; N,N',N''-triethylenethiophosphoramide. Heretofore, this compound has been prepared from a thiophosphoryl halide and ethyleneimine as set forth in the following reaction scheme:

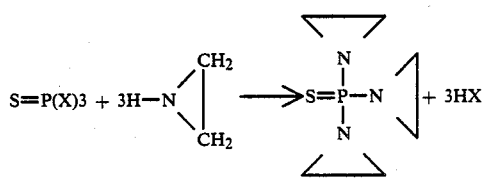

wherein X is chloro or bromo. This reaction is preferably carried out in an organic solvent such as benzene, diethyl ether, dioxane, and the like. It is also necessary to have present an acid acceptor which may be tertiary amine such as triethylamine, N-methylmorpholine or pyridine. The reaction can also be carried out in water or in a substantially aqueous solution in which case acid acceptors are also required to neutralize the hydrohalic acid formed. Under these circumstances, the acid acceptor may be an alkaline substance such as an alkali metal carbonate or bicarbonate. Isolation of the product from the organic solvent may be accomplished by filtration of the tertiary amine hydrohalide salt followed by evaporation of the organic solvent from the filtrate. When the compound is prepared in an aqueous medium, then it may be extracted from the aqueous solution by means of organic solvents. The reaction is generally carried out at a temperature within the range of 0° C. to about 60° C. At this temperature range, the reaction is usually complete within a period of 30 minutes to about 5-6 hours.

Ethyleneimine (aziridine) is a strongly alkaline liquid which polymerizes easily and has an intense odor of ammonia. The $LD_{50}$ orally in rats is only 15 mg./kg. of body of weight, and the F.D.A. has declared this substance a carcinogen. It is strongly irritating to eyes, skin and mucous membranes, and can also be a skin sensitizer. This extremely toxic chemical requires extra-ordinary precautions in use.

It has now been discovered that ethyleneimine can be generated in situ in the preparation of THIOTEPA, thus eliminating the external handling and introduction of this dangerously toxic chemical. The novel process of the present invention is carried out by first cyclizing a β-haloethylamine with an alkali metal hydroxide in aqueous medium. Suitable starting materials are 2-chloroethyamine, 2-bromoethylamine or 2-iodoethylamine, either as the free bases or the acid-addition salts thereof, while suitable bases are NaOH or KOH. This cyclization is carried out by adding an aqueous solution of the β-haloethylamine to an aqueous solution of NaOH or KOH over a period of time of from about 30 minutes to about 2 hours, all at a temperature of −10° C. to +10° C. When the addition is complete, the temperature of the mixture is adjusted to 30° C.-60° C. and the reaction mixture is stirred for 30-90 minutes. The temperature of the reaction mixture is then lowered to −10° to +10° C. and a stoichiometric excess of an alkali metal carbonate or bicarbonate is added, with stirring. This is followed by the addition of a stoichiometric amount of a thiophosphoryl halide, with stirring. The reaction mixture is then stirred for an additional 1-2 hours at −10° C. to +10° C. to complete the conversion to THIOTEPA followed by extraction of the product from the reaction mixture with a suitable water immiscible organic solvent such as benzene, diethyl ether, dioxane, and the like.

The invention will be described in greater detail in conjunction with the following specific example.

EXAMPLE 1

A reactor is charged with 7,700 to 8,300 parts of water, 7,600 to 8,600 parts of anhydrous potassium hydroxide are added and the solution is stirred and cooled to −10° C. to +10° C. While agitating, a solution of 10,400 to 11,400 parts of 2-bromoethylamine hydrobromide in 5,200 to 5,700 parts of water is charged to the reactor over 30 to 90 minutes, while maintaining the temperature at −10° C. to +10° C. When the addition is complete, the temperature is adjusted to 40° C. to 50° C. and the mixture is stirred for 40 to 70 minutes. The temperature is then lowered to −10° C. to +10° C. and 5,000 to 5,700 parts of anhydrous potassium carbonate are added with stirring. The ethylenimine thus generated in situ is further reacted with phosphorus sulfochloride to produce the desired THIOTEPA.

I claim:

1. In a process for producing THIOTEPA wherein thiophosphoryl halide is reacted with ethyleneimine, the improvement which comprises the steps of:
   (a) adding aqueous solution of B-haloethylamine or salt thereof to an aqueous solution of NaOH or KOH with stirring within a temperature range of from about −10° C. to about +10° C.,
   (b) adjusting the temperature of the resulting reaction mixture to from about 30° C. to about 60° C. and stirring for a sufficient period of time to complete the reaction,
   (c) lowering the temperature of the reaction mixture to from about −10° C. to about +10° C. and neutralizing with a stoichiometric excess of an alkali metal carbonate or bicarbonate; providing in situ formation of ethylenimine.

* * * * *